US008832878B2

(12) United States Patent  
McGann

(10) Patent No.: US 8,832,878 B2  
(45) Date of Patent: Sep. 16, 2014

(54) APPARATUSES FOR SUPPORTING A PERSON IN AN UPRIGHT POSITION

(76) Inventor: Bryan Andrew McGann, Raleigh, NC (US)

( * ) Notice: Subject to any disclaimer, the term of this patent is extended or adjusted under 35 U.S.C. 154(b) by 0 days.

(21) Appl. No.: 13/569,268

(22) Filed: Aug. 8, 2012

(65) Prior Publication Data

US 2013/0036551 A1 Feb. 14, 2013

Related U.S. Application Data

(60) Provisional application No. 61/522,340, filed on Aug. 11, 2011.

(51) Int. Cl.
| A61G 13/12 | (2006.01) |
| A61F 5/37 | (2006.01) |
| A47C 21/08 | (2006.01) |
| A47C 20/02 | (2006.01) |

(52) U.S. Cl.
CPC .............. *A47C 20/027* (2013.01); *A61F 5/3784* (2013.01); *A47C 21/08* (2013.01)
USPC ........................ 5/621; 5/624; 5/659; 128/96.1

(58) Field of Classification Search
USPC ........... 5/621, 624, 659; 297/465; 602/32, 33, 602/36, 38; 128/96.1, 98.1, 99.1, 101.1, 128/875
See application file for complete search history.

(56) References Cited

U.S. PATENT DOCUMENTS

| 2,308,466 A | 1/1943 | Johnson |
| 2,940,443 A | 6/1960 | Baker |
| 2,991,785 A | 7/1961 | Terrell |
| 3,612,605 A | 10/1971 | Posey, Jr. |
| 4,161,946 A | 7/1979 | Zuesse |

(Continued)

FOREIGN PATENT DOCUMENTS

| FR | 9606620 A1 | 5/1996 |
| FR | 2748920 A1 | 11/1997 |

(Continued)

OTHER PUBLICATIONS

International Search Report and Written Opinion mailed Feb. 14, 2013, for corresponding Int'l. patent application No. PCT/US12/49892 filed Aug. 8, 2012, references cited herein.

(Continued)

*Primary Examiner* — Peter M Cuomo  
*Assistant Examiner* — Brittany Wilson  
(74) *Attorney, Agent, or Firm* — Olive Law Group, PLLC

(57) ABSTRACT

Disclosed herein are apparatuses for supporting a person in an upright position while sleeping or resting in a bed such that the person can avoid sliding down into a horizontal position as a result of natural forces of gravity and normal movement during sleep. According to an aspect, an apparatus includes a harness configured to hold a person, an anchor to secure the harness to a bed, and a tether having one end connected to the harness and another end connected to the anchor. The anchor can include a support member and an insert extending from the support member such that the upper surface of the insert comes into contact with a mattress and the lower surface of the insert comes into contact with a bed-base. The apparatus can hold the person in the same position on the bed allowing them to remain upright while sleeping or resting.

15 Claims, 9 Drawing Sheets

(56) References Cited

U.S. PATENT DOCUMENTS

| | | |
|---|---|---|
| 4,267,830 A | 5/1981 | Vick |
| 4,536,903 A | 8/1985 | Parker |
| 4,742,821 A | 5/1988 | Wootan |
| 4,853,996 A | 8/1989 | Harrigan et al. |
| 4,911,105 A | 3/1990 | Hocum |
| 4,958,644 A | 9/1990 | Rodgers |
| 5,042,878 A | 8/1991 | Collins |
| 5,154,487 A | 10/1992 | Warburton |
| 5,267,352 A | 12/1993 | Rodarmel |
| 5,333,523 A | 8/1994 | Palm |
| 5,397,171 A | 3/1995 | Leach |
| 5,400,803 A | 3/1995 | Vines |
| 5,401,236 A | 3/1995 | Summerville |
| 5,829,443 A | 11/1998 | Cunningham |
| 6,007,156 A | 12/1999 | Chang |
| 6,224,154 B1 | 5/2001 | Stoki |
| 6,240,581 B1 | 6/2001 | Pender |
| 6,402,251 B1 | 6/2002 | Stoll |
| 6,834,405 B1 | 12/2004 | Hillstead |
| 6,857,149 B2 | 2/2005 | Hoggatt et al. |
| 6,931,683 B1 | 8/2005 | Elkin et al. |
| 7,044,267 B2 | 5/2006 | Sigler |
| 7,093,413 B1 | 8/2006 | Hughes |
| 7,144,085 B2 | 12/2006 | Vits et al. |
| 7,210,176 B2 | 5/2007 | Weedling et al. |
| 7,251,846 B1 | 8/2007 | Elkin et al. |
| 7,282,039 B2 | 10/2007 | Henke |
| 7,296,311 B1 * | 11/2007 | Navarrette ............... 5/507.1 |
| 7,644,990 B2 | 1/2010 | Pearson |
| 7,654,973 B2 | 2/2010 | Firsov |
| 7,758,130 B2 | 7/2010 | Jay |
| 2004/0026979 A1 | 2/2004 | Haddon |
| 2005/0172408 A1 | 8/2005 | Temple |
| 2005/0194830 A1 | 9/2005 | Kohani |
| 2008/0060873 A1 | 3/2008 | Lang et al. |
| 2009/0152932 A1 | 6/2009 | Rothschild |
| 2010/0038953 A1 | 2/2010 | Collins et al. |
| 2010/0175702 A1 | 7/2010 | West |
| 2010/0235996 A1 | 9/2010 | King |
| 2010/0287706 A1 | 11/2010 | Nour |
| 2011/0078859 A1 | 4/2011 | North |

FOREIGN PATENT DOCUMENTS

| | | |
|---|---|---|
| FR | 0404421 A1 | 10/2005 |
| GB | 2314261 A | 12/1997 |
| GB | 2450314 A | 12/2008 |
| JP | 57-152135 U | 9/1982 |

OTHER PUBLICATIONS

International Preliminary Report on Patentability mailed Feb. 11, 2014, for corresponding Int'l. patent application No. PCT/US12/49892, references previously cited.

Notification Concerning Transmittal of IPRP (Form PCT/IB/326) mailed Feb. 20, 2014, for corresponding Int'l. patent application No. PCT/US12/49892.

* cited by examiner

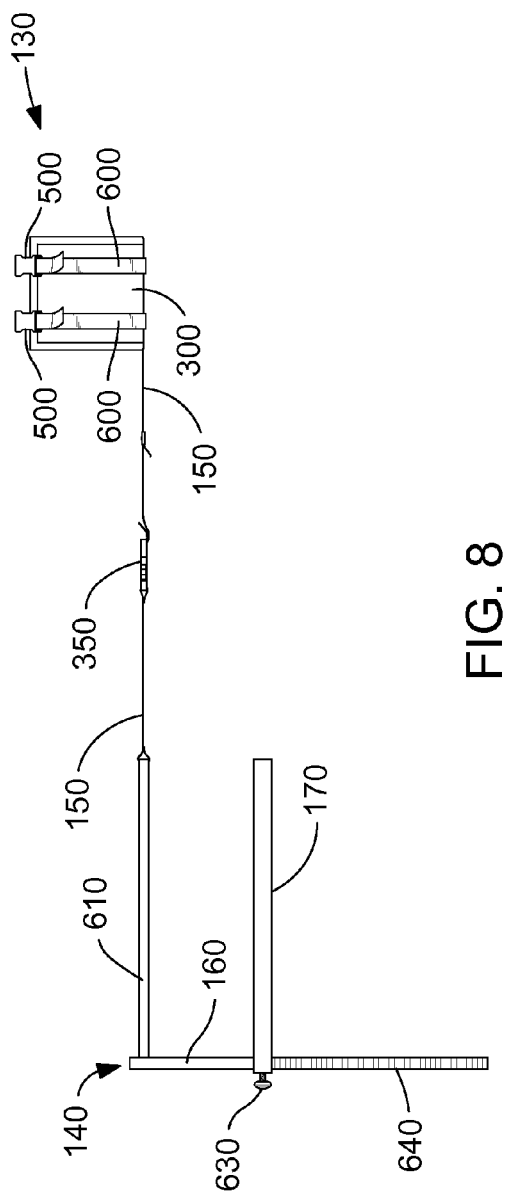
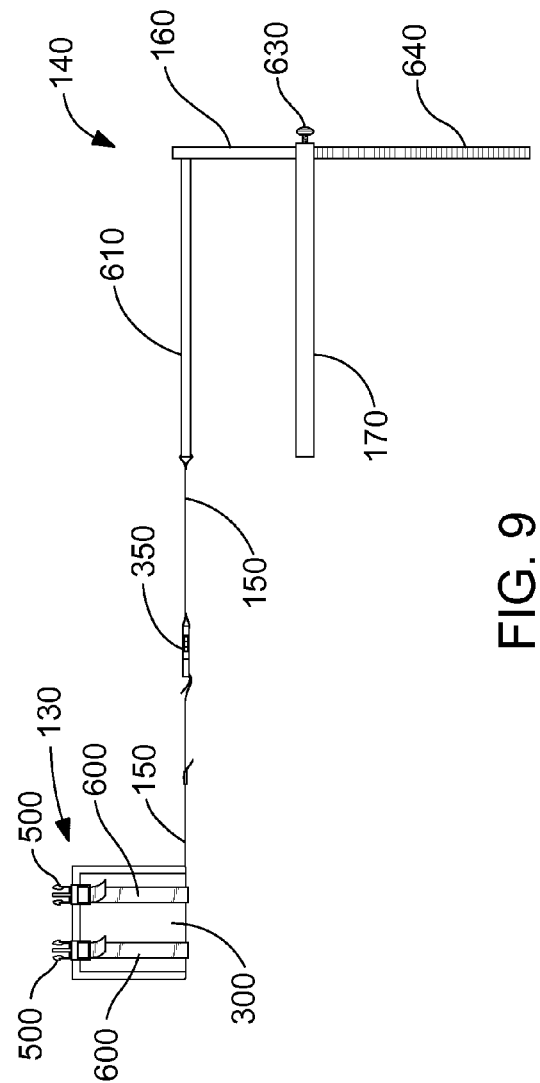
FIG. 8
FIG. 9

APPARATUSES FOR SUPPORTING A PERSON IN AN UPRIGHT POSITION

CROSS REFERENCE TO RELATED APPLICATION

This application claims the benefit of U.S. Provisional Patent Application No. 61/522,340, filed Aug. 11, 2011 and titled DEVICE ALLOWING HUMANS TO REMAIN UPRIGHT WHILE SLEEPING IN A BED, the content of which is hereby incorporated herein by reference in its entirety.

TECHNICAL FIELD

This disclosure is related to an apparatus for supporting a person in an upright position in a bed and, more particularly, toward an apparatus for supporting a person in an upright position while they are sleeping or resting in a bed or unable to remain upright due to any condition including lack of strength or injury.

BACKGROUND

There are instances when it is beneficial for a person to sleep in an upright position, or more specifically to sleep while lying on one's back with the head and chest higher than the waist and legs. Such instances can include, for example, after upper body surgery, or as a result of a gastro-intestinal ailment, sleep apnea, or other medical conditions or procedures that can require a person to sleep upright to promote healing or prevent further damage to the body. Even if an individual props themselves up in bed with pillows, over time, the weight of the individual and the degree of incline in which they wish to remain work with gravity to return the individual to a supine position with the head and chest essentially at the same level as the waist and legs. In addition, once a person goes to sleep, the natural movement of the body also causes the person to slide down to a more horizontal position. Other methods of sleeping upright, such as a reclining chair, are expensive and uncomfortable and often do not allow for the deep sleep necessary for a compromised or infirmed person to heal.

Accordingly, there is a need for an apparatus that can prevent a person from sliding down while sleeping in an upright position and maintain the person in the desired degree of incline.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein are apparatuses for supporting a person in an upright position while sleeping. According to one or more embodiments, an apparatus can include a harness configured to hold a person. The apparatus can also include an anchor that has a support member and an insert extending from the support member such that the insert defines a mattress-facing upper surface and a bed-base-facing lower surface. The apparatus can include a tether including a first end connected to the harness and a second end connected to the anchor.

According to one or more embodiments, an insert can include a U-shaped rod.

According to one or more embodiments, an anchor can include a clamp that extends from the support member and defines a mattress-facing lower surface for clamping the anchor to the mattress. The anchor can include a clamp adjustment mechanism for adjusting a distance between the insert and the clamp. The clamp adjustment mechanism can include a locking pin mechanism.

According to one or more embodiments, a tether can define a length of about 3 to about 5 feet or a length of about 4 feet. The tether can include a length adjustment mechanism for adjusting the length of the tether. The tether can include an attachment mechanism for detachment and attachment of the harness to the anchor. The attachment mechanism can include one of a clip, a buckle, a snap, or a hook and loop fastener.

According to one or more embodiments, the harness can include a belt. The belt can include an attachment mechanism including one of a clip, a buckle, a snap, or a hook and loop fastener for attaching the ends of the belt. The belt can include a front section and a rear section, and the harness can further include a transverse section that connects the front section and the rear section of the belt. The transverse section can include an attachment mechanism for attachment to the belt. The attachment mechanism can include one of a clip, a buckle, a snap, or a hook and loop fastener.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings:

FIG. 8 is a side view of the apparatus shown in FIG. 6;

FIG. 9 is the opposing side view from FIG. 8 of the apparatus shown in FIG. 6;

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different elements similar to the ones described in this document, in conjunction with other present or future technologies.

Figure 1:
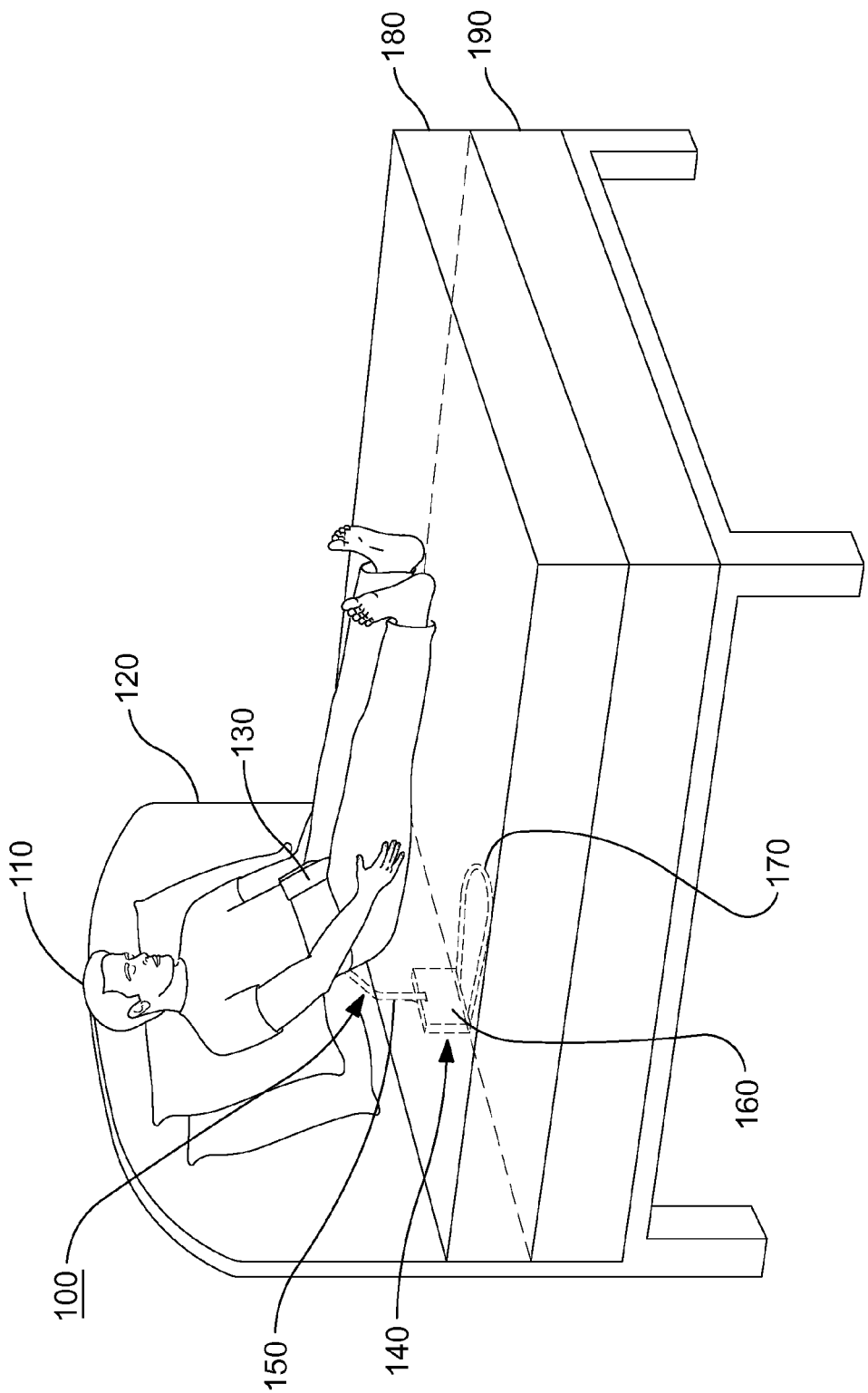
FIG. 1 is a perspective view of an apparatus for supporting a person in an upright position while sleeping or resting in bed in accordance with embodiments of the present disclosure.

FIG. 1 is a perspective view of an apparatus 100 for supporting a person 110 in an upright position while sleeping or resting in a bed 120 in accordance with embodiments of the present disclosure. In addition to supporting persons 110 in an upright position who are asleep, the apparatus 100 is helpful to any person 110 desiring to remain upright in bed 120 are but unable due to any condition including a lack of strength or injury. The apparatus 100 is configured to allow a person 110 to remain in an upright position while sleeping or resting in their own bed 120. The apparatus 100 can include a comfortable harness 130 configured to hold a person 110 by wrapping around the midsection of the person 110, an anchor 140 to secure the harness to the bed, and a tether 150 having one end connected to the harness 130 and the other end connected to the anchor 140. The anchor 140 can include a support member 160 and an insert 170 extending from the support member 160 such that the upper surface of the insert 170 comes into contact with the mattress 180 and the lower surface of the insert comes into contact with the bed-base 190. For purposes of the specification and claims, the term "bed-base" may refer to the part of a bed that supports a mattress. The term bed-base is meant to refer to a "foundation" or a "box spring" or "spring slats" or any other term used to describe the part of a bed that supports a mattress. The anchor 140 is configured at the head of the bed 120 such that the insert 170 is positioned underneath the mattress 180 and on top of the bed-base 190. The support member 160 of the anchor 140 is positioned between the bed 120 and the mattress 180. In this manner, the apparatus 100 can hold the person 110 in the same position on the bed 120 allowing them to remain upright while sleeping. As a result of being in the harness 130 and the harness 130 being secured to the bed 120 through the tether 150 attached to the anchor 140, the weight of the person, and the natural movements of a person during sleep, 110 no longer cause them to slide down into a horizontal position. As long as the person 110 remains in the apparatus 100, even sleeping will not cause the person 110 to slide down in the bed 120 and the person's 110 desired degree of incline can be maintained.

Figure 2:
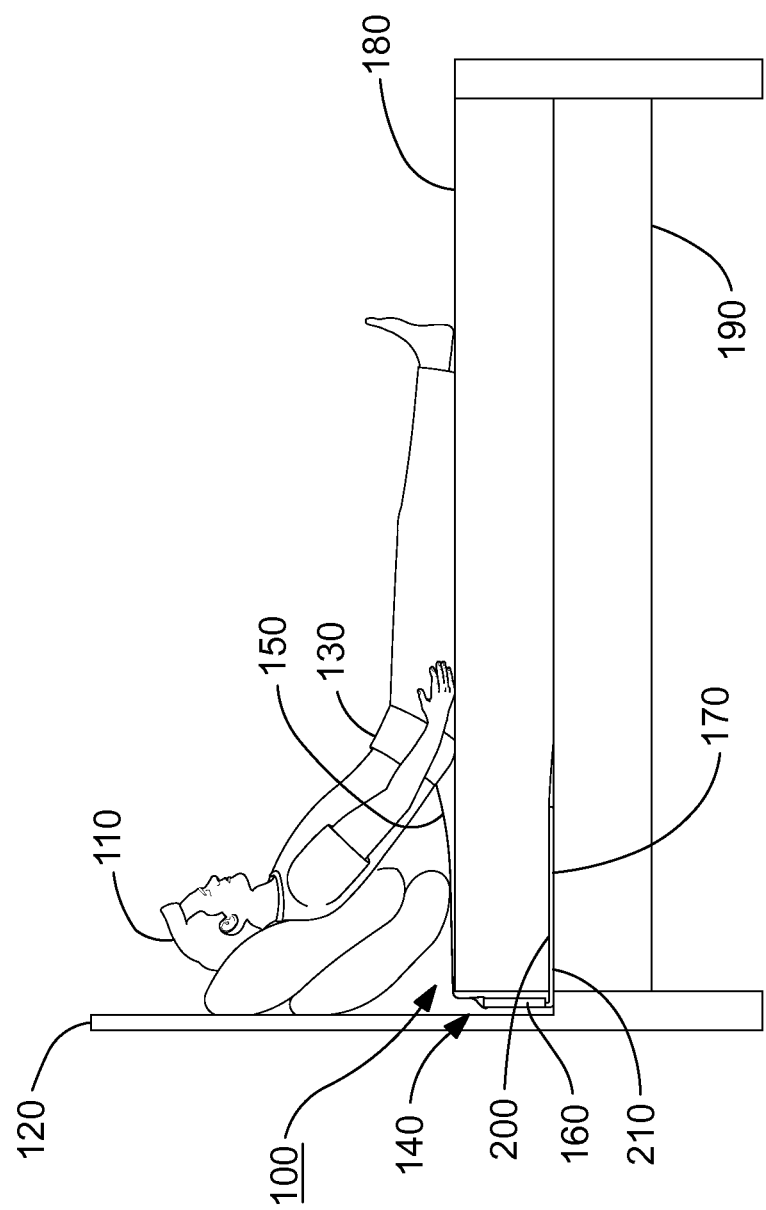
FIG. 2 is a side view of the apparatus shown in FIG. 1.

FIG. 2 is a side view of the apparatus 100 for supporting the person 110 sleeping in an upright position in the bed 120 in accordance with embodiments of the present disclosure. FIG. 2 illustrates the upper surface of the insert 170 as mattress-facing upper surface 200 and the lower surface of the insert 170 as bed-base facing lower surface 210.

Figure 3:
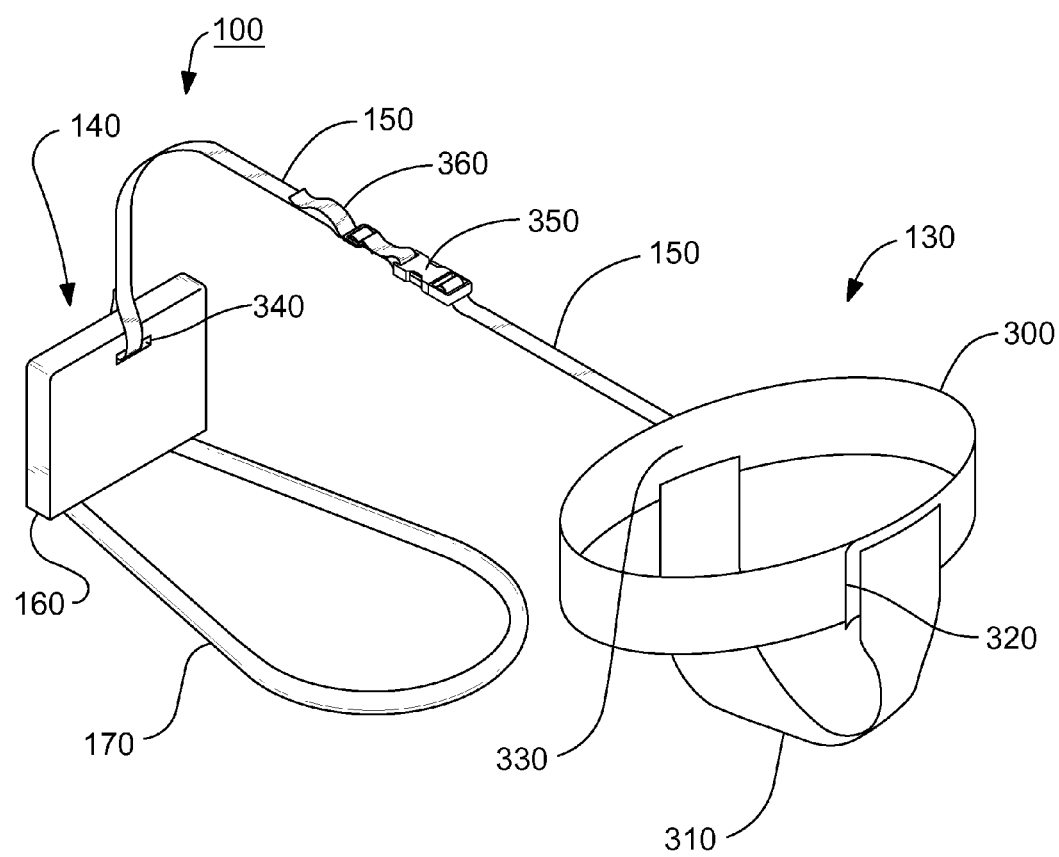
FIG. 3 is a perspective view of the apparatus shown in FIG. 1.

FIG. 3 is a perspective view of apparatus 100 for supporting the person 110 in an upright position in the bed 120 in accordance with embodiments of the present disclosure. The harness 130 is configured to wrap around the midsection of the person 110 shown in FIGS. 1 and 2 and can also in certain embodiments be referred to herein for purposes of the specification and claims as a "belt" 300. The harness 130 or belt 300 can be suitably sized to accommodate different sized persons and can range, for example, between about 4 inches and about 8 inches in width or between about 4 inches and about 5 inches in width. The length of the harness 130 or belt 300 can be suitably sized depending on the size of the person using the apparatus 100, and in general the length can range between about 30 and about 50 inches. The harness 130 can include a transverse section 310 that extends between the legs of the person 110 and connects the front section of the belt 320 to the rear section of the belt 330. The harness 130, belt 300, and transverse section 310 can be made of a soft but durable material, including but not limited to a material such as, for example, neoprene or cloth. The harness 130, belt 300, and transverse section 310 can be made of a material that is lightweight, flexible yet sturdy, and tear resistant. The harness 130 or belt 300 can include a variety of designs configured for persons who need more or less support depending on body type, weight, and sleeping preferences.

On the other end of the support apparatus 100, the anchor 140 can be a rigid object and can be made of any suitable hard material including, but not limited to, metal, stainless steel, plastic, and thermoplastic, such as, for example, nylon, polyoxymethylene (POM), acetal, polyacetal, and polyformaldehyde. In addition, the insert 170 extending from the support member 160 of the anchor 140 can define a wide variety of shapes. For example, the insert 170, can be in the shape of a "U" shaped rod.

The tether 150 of the support apparatus 100 can be made of any suitable durable material such as, for example, nylon, cloth, polyester, cotton, burlap, wool, or any natural or man-made material that is suitable for securing the attachment of the harness 130 to the anchor 140. The tether 150 can be connected to the support member 160 of the anchor 140 through a slot 340 defined within the support member 160. The tether 150 can be attached to the support member slot 340 using any suitable mechanism such as, for example, folding the tether material over and stitching the tether material. The tether 150 can be attached to the rear section of the harness 330 using any suitable mechanism such as, for example, by stitching the tether 150 to the harness 330. The tether 150 of the support apparatus 100 can include an attachment mechanism 350 for detachment and attachment of the harness 130 to the anchor 140. The attachment mechanism 350 can include, but is not limited to, one or more of clips, buckles, snaps, or hook and loop fasteners. For example, the clip attachment mechanism 350 can be configured with a male end of the clip on the tether 150 connected to the harness 130 and a female end of the clip on the tether 150 connected to the anchor 140 such that the harness 130 and anchor 140 can be attached and detached using the clip. The forgoing example is not meant to be limiting, as it would be equally advantageous for the male end of the clip to be attached to the anchor 140 and the female end of the clip to be attached to the harness 130.

Figures 4, 5:
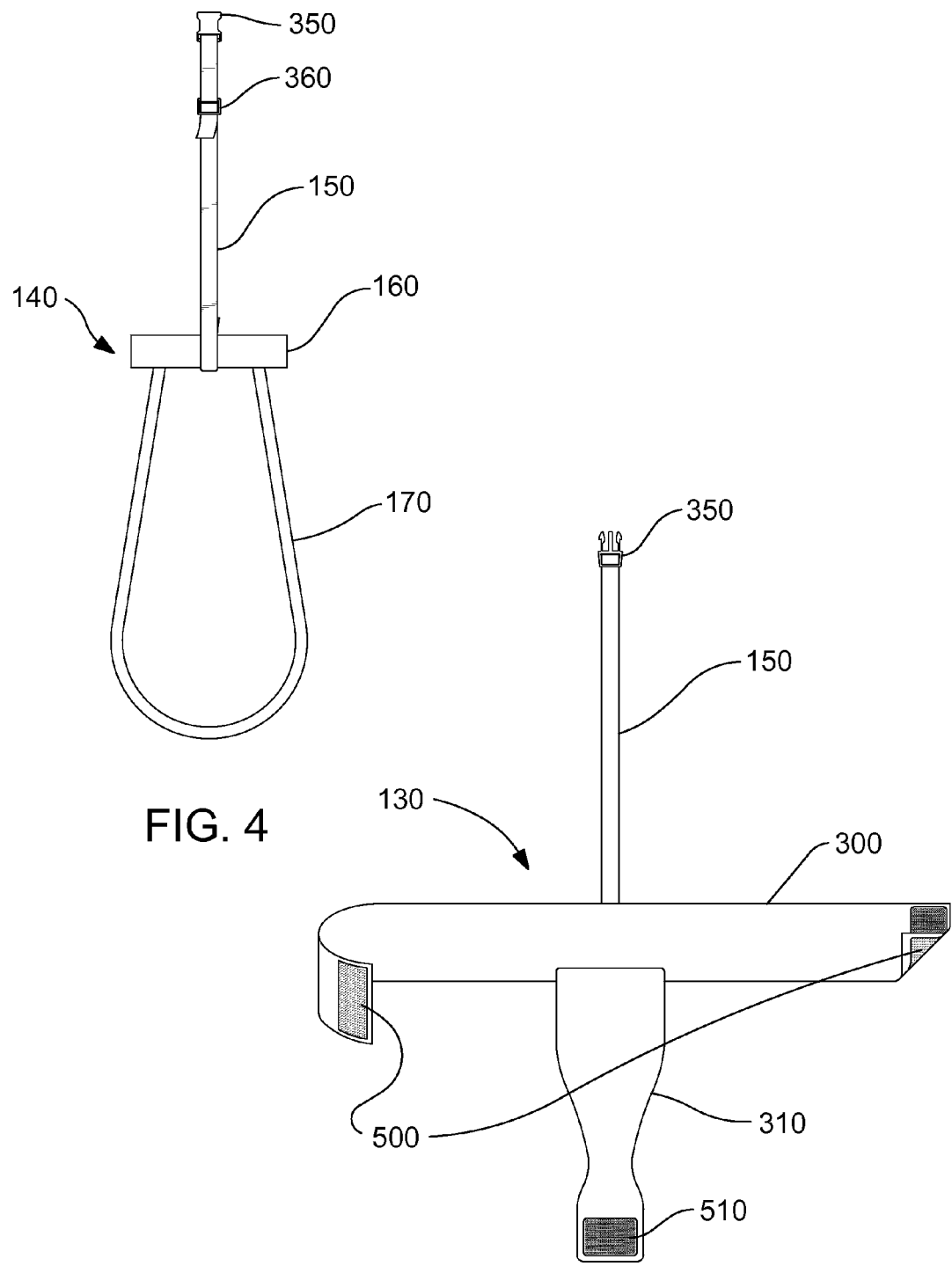
FIG. 4 is a top view of an anchor and the tether of the apparatus shown in FIG. 1.
FIG. 5 is a top view of a harness with an attached tether of the apparatus shown in FIG. 1.

FIG. 4 is a top view of anchor 140 and also illustrates tether 150 connected to anchor 140 and detached from harness 130 using attachment mechanism 340 in accordance with embodiments of the present disclosure. The length of the tether 150 can range from about 3 feet to about 5 feet. In addition, the tether 150 can include a length adjustment mechanism 360 for adjusting a length of the tether 150.

FIG. 5 is a top view of harness 130 with attached tether 150 in accordance with embodiments of the present disclosure. The harness 130 or belt 300 can include an attachment mechanism 500 for attaching the ends of the belt 300 together. The attachment mechanism 500 can include, but is not limited to, one or more of clips, buckles, snaps, or hook and loop fasteners. For example, the belt attachment mechanism 500 can be configured with hook fasteners on a first end of the belt and configured with loop fasteners on the other end of the belt for attaching the ends of the belt together. The transverse section 310 of the harness 130 can include an attachment mechanism 510 for attachment of the transverse section 310 to the front section of the belt 320.

Figure 6:
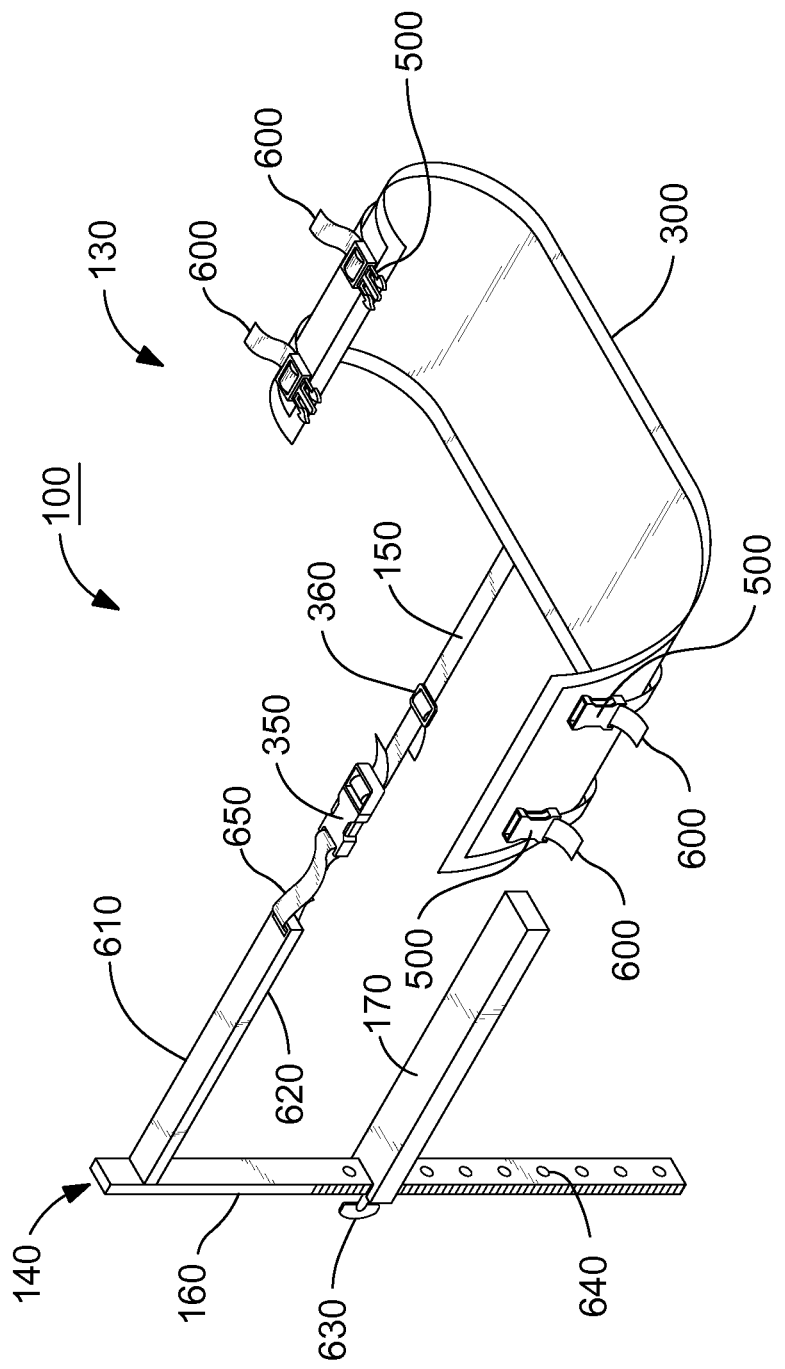
FIG. 6 is a perspective view of another apparatus for supporting a person sleeping in an upright position in bed in accordance with embodiments of the present disclosure.

FIG. 6 is a perspective view of another apparatus 100 for supporting the person 110 sleeping in an upright position in the bed 120 in accordance with embodiments of the present disclosure. As illustrated in FIG. 5 and described herein above, the ends of the harness 130 or belt 300 can be attached using belt attachment mechanism 500. The attachment mechanism 500 can include one or more of clips, buckles, snaps, or hook and loop fasteners. For example, the ends of the harness 130 or belt 300 can be attached using an attachment mechanism 500 in which clips are attached to the harness 130 or belt 300 by straps 600. The attachment mechanism clips 500 can be configured with a male end and a female end such that the clips 500 can be joined together to cause the straps 600 to connect together as one. The clips 500 are configured such that the straps 600 can be adjusted in length by pulling the straps 600 tighter through the clips 500, or loosening the straps 600 through the clips 500. The clips 500 can be made of a rigid material such as, for example, any suitable hard material including metal, stainless steel, plastic, and thermoplastic, such as, for example, nylon, polyoxymethylene (POM), acetal, polyacetal, and polyformaldehyde. The straps 600 can be made of a material such as nylon or other foldable, flat material allowing for the connection of the belt 300 or harness 130 to the clips 500. The strap 600 material can be formed into a flat structure such that the straps 600 do not interfere with the comfort of the person 110 using the apparatus 100 and positioned above the strap 600. The straps 600 can be made of any suitable durable material including but not limited to nylon, cloth, polyester, cotton, burlap, wool, or any natural or man-made material.

FIG. 6 further illustrates the anchor 140 attached to the harness 130 of apparatus 100 for supporting the person 110 sleeping in an upright position in the bed 120 in accordance with embodiments of the present disclosure. The anchor 140 shown in FIG. 6 includes a clamp 610 in addition to insert 170. The clamp 610 extends from the support member 160 and defines a mattress-facing lower surface 620 for clamping the anchor 140 to the mattress 180. The anchor 140 illustrated in FIG. 6 is configured at the head of the bed 120 such that the clamp 610 is positioned on top of the mattress 180 and the insert 170 is positioned underneath the mattress 180. The insert 170 can be configured to include an adjustment mechanism 630 for adjusting a distance between the insert 170 and the clamp 610 to secure the anchor 140 to the mattress 180. The insert 170 can be vertically adjustable along the support member 160 by utilizing a locking pin 630 or similar type fastener 630 as the adjustment mechanism 630. The locking pin adjustment mechanism 630 can be configured such that a rigid locking pin can be extended into pre-cut holes 640 in the lower portion of the support member 160. These pre-cut holes 640 can be spaced such that different thicknesses of mattress 180 can be utilized with the apparatus 100. The clamp 610, similar to the insert 170, can define a wide variety of shapes. The tether 150 can be attached to the anchor 140 through the clamp 610 using any suitable attachment mechanism 650 such as, for example, folding the tether material over and stitching the tether 150 to the clamp 610. When the anchor 140 is configured at the head of the bed 120 as described above, such that the tether 150 is connected to the clamp 610 on one end and the belt 300 or harness 130 on the other end, support is provided for the person 110 using the apparatus 100 to remain sleeping upright in the bed 110.

Figure 7:
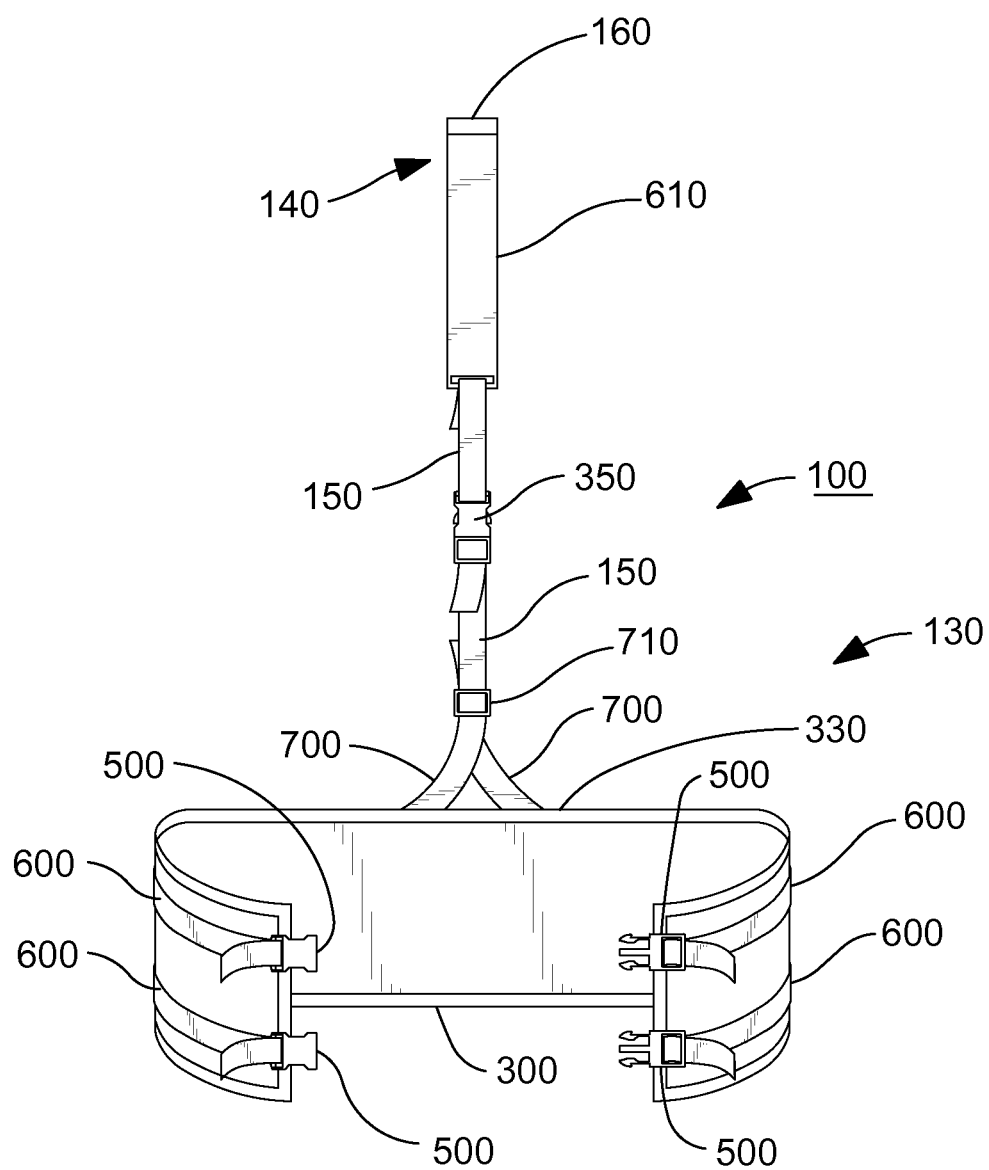
FIG. 7 is a top view of the apparatus shown in FIG. 6.

FIG. 7 is a top view of apparatus 100 for supporting the person 110 in an upright position in the bed 120 in accordance with embodiments of the present disclosure. As illustrated in FIG. 7, the tether 150 that attaches the anchor 140 to the harness 130 can define a "Y" shape 700 at the end in which the tether 150 is attached to the rear section of the harness 330. The base of the Y-shaped tether 700 can be connected to the tether 150 by a tether connector 710. The Y-shaped tether 700 can be attached to the tether 150 through the tether connector 710 using any suitable mechanism including, but not limited to, a buckle or by stitching. The Y-shaped tether 700 can be attached to the rear section of the harness 330 using any suitable mechanism such as, for example, stitching the Y-shaped tether 700 to the harness 330. The Y-shaped tether 700 provides support to the person 110 using the apparatus 100 to sleep in an upright position.

FIG. 8 is a side view of apparatus 100 for supporting the person 110 in an upright position sleeping in the bed 120 in accordance with embodiments of the present disclosure. The anchor 140 depicted in FIG. 8 includes the clamp 610 for securing the anchor 140 to the mattress 180. In FIG. 8, the attachment mechanism 500 used for attaching the ends of the harness 130 is clips and the male ends of the clips are shown. FIG. 9 is the opposing side view of apparatus 100 for supporting the person 110 in an upright position sleeping in the bed 120 in accordance with embodiments of the present disclosure. In FIG. 9, the female ends of the clips of attachment mechanism 500 for attaching the ends of the harness 130 are depicted.

Figure 10:
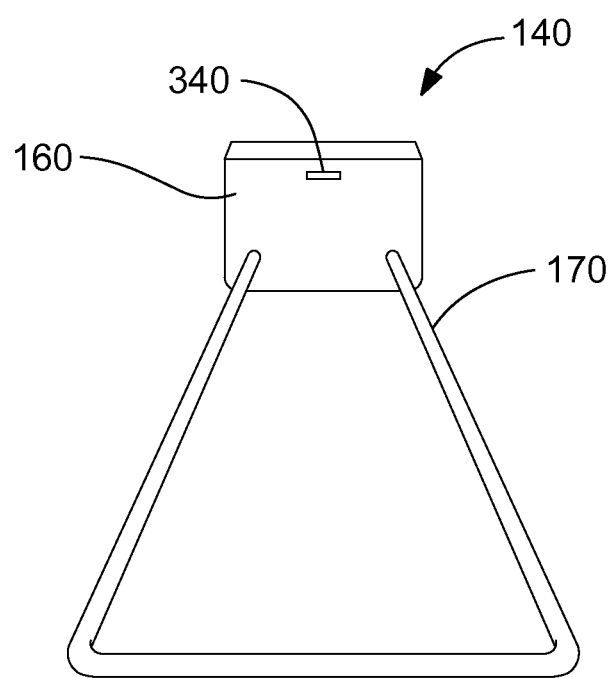
FIG. 10 is a perspective view of another anchor of an apparatus for supporting a person in an upright position sleeping in bed in accordance with embodiments of the present disclosure.

FIG. 10 is a perspective view of the anchor 140 of the apparatus 100 for supporting the person 110 in an upright position in the bed 120 in accordance with embodiments of the present disclosure. The insert 170 of anchor 140 depicted in FIG. 10 is in the shape of a "U" shaped rod. Alternatively, the insert 170 may be any other suitable shape or size.

Figure 11:
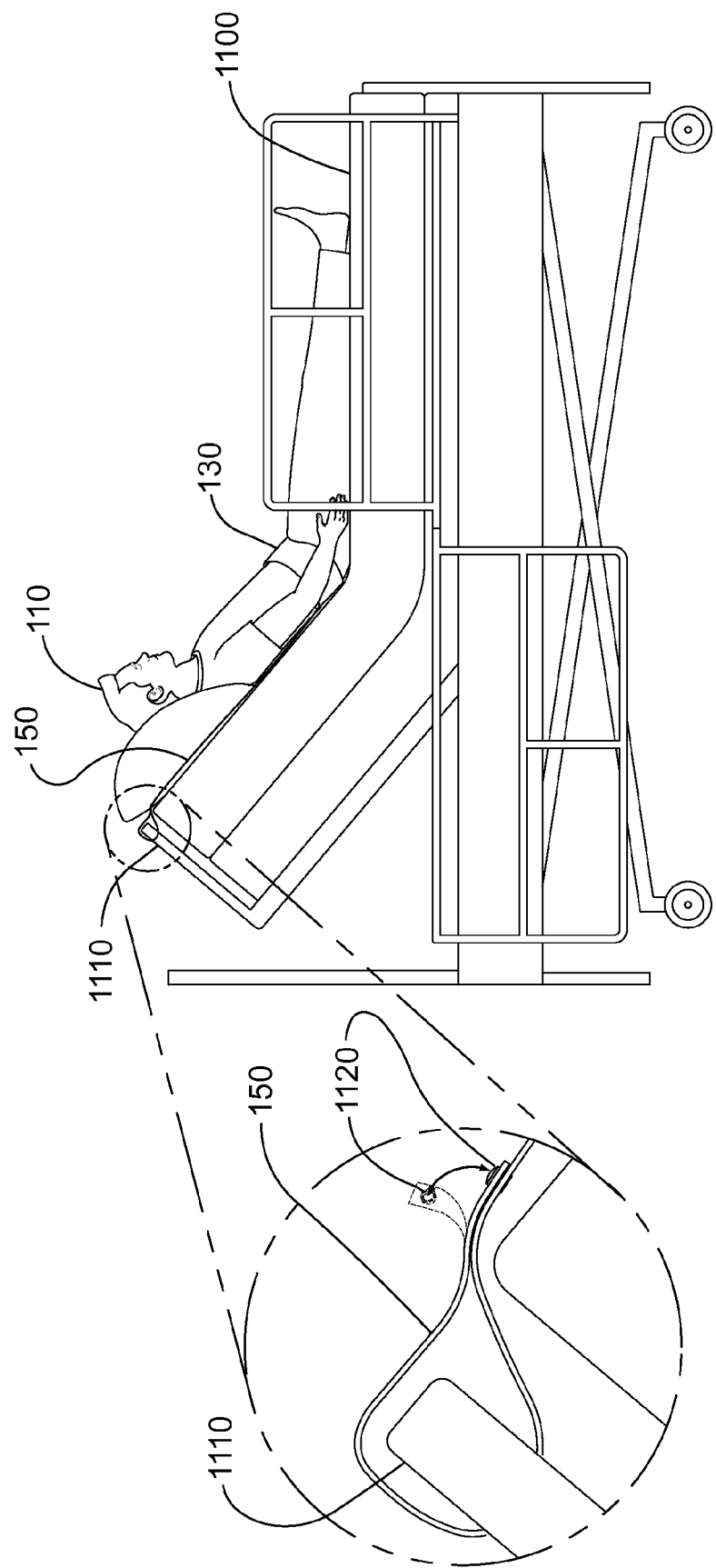
FIG. 11 is a side view of a person in an upright position sleeping in a hospital-type bed using a harness in which the harness is attached to a tether, and the tether is attached directly to the bed in accordance with embodiments of the present disclosure.

In one or more embodiments, the presently disclosed subject matter provides an apparatus for supporting a person 110 in an upright position while sleeping or resting in a mechanical or hospital-type bed. FIG. 11 is a side view of the person 110 in an upright position sleeping in a hospital-type bed 1100 using harness 130 in which harness 130 is attached to tether 150 and tether 150 is attached directly to the bed 1100 in accordance with embodiments of the present disclosure. The tether 150 can be attached directly to the bed 1100 by looping the tether 150 around a support member 1110 of the bed 1100 and securing the end of the tether 150 back against itself using any suitable attachment mechanism 1120. The attachment mechanism 1120 for securing the end of the tether 150 to the support member 1110 can include a snap mechanism, a buckle, a clip, a hook and loop fastener or another suitable type of fastener. The specific location of the attachment of the tether 150 to the support member 1110 of the bed 1100 will depend on the design and brand of bed 1100.

The person 110 can use the apparatus 100 by positioning the anchor 140 at the head end of the bed 120 such that the insert 170 is positioned underneath the mattress 180 and on top of the bed-base 190. The support member 160 of the anchor 140 is positioned between the bed 120 and the mattress 180. If the person 110 is using apparatus 100 that includes anchor 140 having a clamp 610, the person can adjust the distance between insert 170 and clamp 610 using adjustment mechanism 630 such that the mattress 180 is secured snuggly between the insert 170 and clamp 610. The person 110 can adjust the tether 150 length to fit his height and desired sleeping position. The person 110 can attach the harness 130 to the tether 150 using the attachment mechanism 350. Subsequently, the person 110 can lie down in the bed 120 and affix the harness 130 around his waist and secure the harness 130 using the attachment mechanism 500. If the attachment mechanism 500 includes clips and adjustable straps 600, the person 110 can adjust the harness 130 by pulling the straps 600 through the clips. Once the person 110 is in the harness 130 of the apparatus 100 the gravity-caused pressure against the mattress 180 will then secure the person 110 in an upright position for sleeping.

Features from one embodiment or aspect may be combined with features from any other embodiment or aspect in any appropriate combination. For example, any individual or collective features of method aspects or embodiments may be applied to apparatus, system, product, or component aspects of embodiments and vice versa.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. An apparatus for supporting a person in an upright position, the apparatus comprising:
    a harness configured to hold a person;
    an anchor comprising:
        a support member; and
        an insert extending from the support member and defining a mattress-facing upper surface and a bed-base-facing lower surface, wherein the insert comprises a rod having first and second ends that are attached to the support member; and
        a tether including a first end connected to the harness and a second end connected to the anchor;
        a clamp extending from the support member and defining a mattress-facing lower surface for clamping the anchor to a mattress, and
    wherein the anchor comprises a clamp adjustment mechanism for adjusting a distance between the insert and the clamp.

2. The apparatus of claim 1, wherein the clamp adjustment mechanism comprises a locking pin mechanism.

3. The apparatus of claim 1, wherein the tether defines a length ranging from 3 to 5 feet.

4. The apparatus of claim 1, wherein the tether defines a length adjustment mechanism for adjusting a length of the tether.

5. The apparatus of claim 1, wherein the tether comprises an attachment mechanism for detachment and attachment of the harness to the anchor.

6. The apparatus of claim 5, wherein the attachment mechanism comprises one of a clip, a buckle, a snap, or a hook and loop fastener.

7. The apparatus of claim 1, wherein the harness comprises a belt.

8. The apparatus of claim 7, wherein the belt comprises an attachment mechanism comprising one of a clip, a buckle, a snap, or a hook and loop fastener for attaching ends of the belt.

9. The apparatus of claim 7, wherein the belt comprises a front section and a rear section, and
    wherein the harness further comprises a transverse section that connects the front section and the rear section of the belt.

10. The apparatus of claim 9, wherein the transverse section comprises an attachment mechanism for attachment to the belt.

11. The apparatus of claim 10, wherein attachment mechanism comprises one of a clip, a buckle, a snap, or a hook and loop fastener.

12. An apparatus for supporting a person in an upright position, the apparatus comprising:
    a harness configured to hold a person;
    an anchor comprising:
        a support member; and
        an insert extending from the support member and defining a mattress-facing upper surface and a bed-base-facing lower surface; and
        a tether including a first end connected to the harness and a second end connected to the anchor,
        a clamp extending from the support member and defining a mattress-facing lower surface for clamping the anchor to a mattress, and
    wherein the anchor comprises a clamp adjustment mechanism for adjusting a distance between the insert and the clamp.

13. The apparatus of claim 12, wherein the clamp adjustment mechanism comprises a locking pin mechanism.

14. The apparatus of claim 1, wherein the harness comprises a belt.

15. The apparatus of claim 14, wherein the belt comprises a front section and a rear section, and
    wherein the harness further comprises a transverse section that connects the front section and the rear section of the belt.

* * * * *